United States Patent [19]

Singer et al.

[11] Patent Number: 4,720,534
[45] Date of Patent: Jan. 19, 1988

[54] NCO-TERMINATED COMPOUNDS FROM ADDUCTS OF MERCAPTO-FUNCTIONAL POLYHYDRIC ALCOHOLS AND VINYL-TYPE SILANES CONTAINING HYDROLYZABLE GROUPS

[75] Inventors: Debra L. Singer, Pittsburgh; Rostyslaw Dowbenko, Gibsonia, both of Pa.

[73] Assignee: PPG Industries, Inc., Pittsburgh, Pa.

[21] Appl. No.: 920,396

[22] Filed: Oct. 20, 1986

Related U.S. Application Data

[62] Division of Ser. No. 816,079, Jan. 3, 1986, Pat. No. 4,652,664.

[51] Int. Cl.$^4$ ............................................. C08G 77/04
[52] U.S. Cl. ...................................... 528/28; 528/32; 556/419; 556/420; 556/422
[58] Field of Search .................... 528/28, 32; 556/420, 556/419, 422

[56] References Cited

U.S. PATENT DOCUMENTS 4,652,664  3/1987  Singer et al. ......................... 528/28

Primary Examiner—Melvyn I. Marquis
Attorney, Agent, or Firm—Thomas M. Breininger

[57] ABSTRACT

Disclosed is a free-radical addition product of a mercapto-functional polyhydric alcohol and a vinyl-type silane having at least one hydrolyzable group directly attached to a silicon atom, the addition product prepared by reacting the mercapto-functional polyhydric alcohol and the vinyl-type silane in the presence of a free radical initiator. The addition product contains at least two hydroxyl groups bonded to carbon atoms and at least one silicon atom bonded to at least one hydrolyzable group.

The resulting polyhydroxyl-functional addition products can be chain extended using organic polyisocyanates to produce isocyanate-terminated compounds which also contain silicon atoms directly bonded to hydrolyzable groups along the molecule chains.

5 Claims, No Drawings

NCO-TERMINATED COMPOUNDS FROM ADDUCTS OF MERCAPTO-FUNCTIONAL POLYHYDRIC ALCOHOLS AND VINYL-TYPE SILANES CONTAINING HYDROLYZABLE GROUPS

This is a division of application Ser. No. 816,079, filed Jan. 3, 1986, now U.S, Pat. No. 4,652,664.

BACKGROUND OF THE INVENTION

Compounds containing silicon atoms bonded to hydrolyzable groups prepared from polyols and isocyanato-functional compounds which also containing silicon atoms bonded to hydrolyzable groups such as gamma-isocyanatopropyl triethoxy silane are known.

The present invention is directed to a new class of addition products which contain contain silicon atoms bonded to hydrolyzable groups and which also contain thio groups. The addition products are derived from mercapto-functional polyhydric alcohols and vinyl-type silanes containing silicon atoms bonded to hydrolyzable groups.

The present invention is also directed to a new class of compounds containing silicon atoms bonded to hydrolyzable groups and which also contain thio groups derived by chain extension of the aforesaid addition products with organic polyisocyanates.

SUMMARY OF THE PRESENT INVENTION

The present invention is for a free-radical addition product of a mercapto-functional polyhydric alcohol and a vinyl-type silane having at least one hydrolyzable group directly attached to a silicon atom, the addition product prepared by reacting the mercapto-functional polyhydric alcohol and the vinyl type silane in the presence of a free radical initiator. An addition product of the invention contains at least two hydroxyl groups bonded to carbon atoms and at least one silicon atom bonded to at least one hydrolyzable group.

The resulting polyhydroxyl-functional addition products can be chain extended using organic polyisocyanates, especially organic diisocyanates, to produce isocyanate-terminated compounds which also contain silicon atoms directly bonded to hydrolyzable groups along the molecule chains.

Accordingly, the present invention is also for an NCO-terminated compound prepared by chain extending: (A) the aforesaid free-radical addition product of a mercapto-functional polyhydric alcohol and a vinyl-type silane having at least one hydrolyzable group directly attached to a silicon atom, with (B) an organic polyisocyanate.

DETAILED DESCRIPTION OF THE INVENTION

An addition product of the invention is a reaction product of a mercapto-functional polyhydric alcohol and a vinyl-type silane having at least one hydrolyzable group, Y, directly attached to a silicon atom, the addition product prepared by reacting the mercapto-functional polyhydric alcohol and the vinyl-type silane in the presence of a free radical initiator.

Examples of groups suitable as the hydrolyzable group Y include: $-OR^1$,

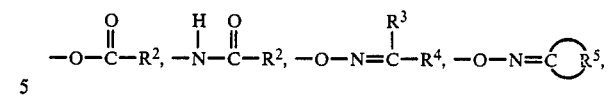

and the monohydroxy and/or cyclic $C_2$-$C_3$ residue of a 1,2- or 1,3-glycol, wherein $R^1$ represents $C_1$-$C_4$ alkyl, $R^2$ independently represents H or $C_1$-$C_4$ alkyl, $R^3$ and $R^4$ independently represent H, $C_1$-$C_4$ alkyl, $C_6$-$C_8$ aryl and $R^5$ represents $C_4$-$C_7$ alkylene.

Preferred hydrolyzable groups include $C_1$-$C_4$ alkoxy groups, and more preferred hydrolyzable groups include methoxy groups.

Illustrative of vinyl-type silanes, having at least one hydrolyzable group directly attached to a silicon atom, which may be utilized for reaction with the mercapto-functional polyhydric alcohol include: vinylalkoxysilanes such as vinyltrimethoxysilane, methylvinyltrimethoxysilane, vinyltriethoxysilane, methylvinyltriethoxysilane, vinylmethyldimethoxysilane, vinylethyldiethoxysilane, and vinyltris(2-methoxyethoxy)silane; vinylacetoxysilanes, such as vinylmethyldiacetoxysilane, vinylethyldiacetoxysilane and vinyltriacetoxysilane; allylalkoxysilanes such as allyltrimethoxysilane, allylmethyldimethoxysilane, and allyltriethoxysilane; divinylalkoxysilanes and divinylacetoxysilanes such as divinyldimethoxysilane, divinyldiethoxysilane and divinyldiacetoxysilane; diallylalkoxysilanes and diallylacetoxysilanes such as diallyldimethoxysilane, diallyldiethoxysilane and diallyldiacetoxysilane; as well as other similar ethylenically unsaturated silane monomers containing one or more hydrolyzable groups. As will be appreciated by one skilled in the art given the present disclosure, use of compounds such as divinyl-group-containing silanes (e.g., divinyldimethoxysilane) and diallyl-group-containing silanes (e.g., diallyldimethoxysilane) can be employed to provide residual vinyl groups (e.g., $-CH=CH_2$) or allyl groups (e.g., $-CH_2-CH=CH_2$) in the addition products as well as the silicon atoms bonded to hydrolyzable groups. It is also possible that more complex structures can be formed, for example, by reaction of both vinyl-type groups on, for example, a divinyl-group-containing silane monomer with mercapto groups on different mercapto-functional monohydric alcohols.

Of the vinyl-type silane monomers described above, the monovinyl-type silane monomers (e.g. vinyltrimethoxysilane or vinylmethyldimethoxysilane as contrasted with divinyl-type silane monomers) are preferred. More preferred vinyl-type silane monomers include vinyl alkoxy silanes especially those having 1 to 4 carbon atoms in the alkoxy group. Particularly preferred vinyl alkoxy silanes are vinyl trialkoxy silanes selected from the group consisting of vinyl trimethoxy silane, vinyl triethoxy silane and a mixture thereof.

It is to be understood that mixtures of vinyl-type silanes having at least one hydrolyzable group directly attached to a silicon atom may be utilized.

The addition product is typically prepared by reacting the vinyl-type silane monomer such as those described above with a mercapto-functional polyhydric alcohol in the presence of a free radical initiator. However, where desired, free radicals may be generated by the action of ultraviolet light or ionizing particle radiation such as electron beam radiation, on compounds containing, for example, suitable ethylenic unsaturation which can generate free radicals upon application of ultraviolet light or ionizing radiation. Typically, however, a free radical initiator is utilized in the preparation of an addition product of the invention. Examples of suitable free radical initiators include: azo compounds such as, for example alpha alpha'-azobis(isobutyronitrile) and 2,2'-azobis(2,4-dimethylvaleronitrile) (available as VAZO 67); peroxides such as benzoyl peroxide and cumene hydroperoxide; and tertiary butyl peracetate, isopropyl percarbonate butyl isopropyl peroxy carbonate and similar compounds. The amount of free radical initiator used generally ranges from 0.1 mole to 1 mole of initiator per mole of mercapto functionality or vinyl-type unsaturation.

Illustrative of suitable mercapto-functional polyhydric alcohols are: thioglycerine (i.e., 1-thioglycerol), 2-thioglycerol, and the like. It is to be understood that mixtures of mercapto-functional polyhydric alcohols may be utilized.

Generally the addition reaction of the vinyl silane monomer with the mercapto-functional polyhydric alcohol is carried out in an organic solvent medium. Organic solvents which may be utilized include virtually any of the organic solvents heretofore employed for vinyl addition reactions such as involved in the solution polymerization of more conventional vinyl-type monomers such as acrylic monomers. Examples of such organic solvents include alcohols, ketones, aromatic hydrocarbons or mixtures thereof. Illustrative of organic solvents of the above type which may be employed are alcohols such as lower alkanols containing 2 to 4 carbon atoms including ethanol, propanol, isopropanol, and butanol; ether alcohols such as ethylene glycol monoethyl ether, ethylene glycol monobutyl ether, propylene glycol monomethyl ether and dipropylene glycol monoethyl ether; ketones such as methyl ethyl ketone, methyl N-butyl ketone, and methyl isobutyl ketone; esters such as butyl acetate; and aromatic hydrocarbons such as xylene, toluene, and naphtha.

The free radical addition reaction of the vinyl-type silane having at least one hydrolyzable group directly attached to a silicon atom with the mercapto-functional polyhydric alcohol is generally carried out in a temperature range of from about 80 to about 120 degrees Celsius, preferably from about 85 to about 95 degrees Celsius depending on the initiator used.

It is believed that the high yield of addition product of the invention which results is attributable at least in part to the fact that the vinyl-type silane monomer, such as the vinyl alkoxy silane monomer, does not tend to homopolymerize in the preparation of the addition product of the invention. Rather it adds essentially 1 to 1 with HS-group of the mercapto-functional polyhydric alcohol in the presence of the free radical initiator.

An addition product of the invention can be chain extended by reaction with an organic polyisocyanate, preferably an organic diisocyanate. An NCO-terminated compound of the invention can be prepared by reacting (A) the aforesaid addition product of a mercapto-functional polyhydric alcohol and a vinyl-type silane having at least one hydrolyzable group directly attached to a silicon atom, with a stoichiometric excess of (B) the organic polyisocyanate.

The organic polyisocyanate may be aromatic, aliphatic, cycloaliphatic, or heterocyclic and may be unsubstituted or substituted with groups such as halogen, etc. Many such organic polyisocyanates are known, examples of which include: toluene-2,4-diisocyanate, toluene-2,6-diisocyanate, and mixtures thereof; diphenylmethane-4,4'-diisocyanate, diphenylmethane-2,4'-diisocyanate and mixtures thereof; para-phenylene diisocyanate; biphenyl diisocyanate; 3,3'-dimethyl-4,4'-diphenyllene diisocyanate; tetramethylene-1,4-diisocyanate; hexamethylene-1,6-diisocyanate; 2,2,4-trimethylhexane-1,6-diisocyanate; lysine methyl ester diisocyanate; bis(isocyanatoethyl)fumarate; isophorone diisocyanate; ethylene diisocyanate; dodecane-1,12-diisocyanate; cyclobutane-1,3-diisocyanate; cyclohexane-1,3-diisocyanate, cyclohexane-1,4-diisocyanate and mixtures thereof; methylcyclohexyl diisocyanate; hexahydrotoluene-2,4-diisocyanate, hexahydrotoluene-2,6-diisocyanate and mixtures thereof; hexahydrophenylene-1,3-diisocyanate, hexahydrophenylene-1,4-diisocyanate and mixtures thereof; perhydrodiphenylmethane-2,4'-diisocyanate, perhydrodiphenylmethane-4,4'-diisocyanate and mixtures thereof. It is to be understood that mixtures of polyisocyanates and monoisocyanates may be utilized as the organic polyisocyanate. Moreover, isocyanate prepolymers may be utilized as the polyisocyanate. Isocyanate prepolymers refer to the reaction products of a polyol and polyisocyanate in which the polyol and polyisocyanate are reacted, by the generally known prepolymer technique, in relative proportions to produce an isocyanato-functional product, namely the isocyanate prepolymer. Also, mixtures of organic isocyanate prepolymers with monomeric isocyanates (so-called semi-prepolymers) may be utilized in the prepolymer technique.

Examples of polyols useful in the preparation of the isocyanate prepolymers include: organic polyols in the broad classes including: (a) simple diols, triols, and higher hydric alcohols; (b) polyester polyols; (c) polyether polyols; (d) amide-containing polyols; (e) acrylic polyols; (f) epoxy polyols; (g) polyhydric polyvinyl alcohols; and (h) urethane polyols.

(a) The simple diols, triols, and higher hydric alcohols are generally known, examples of which include; ethylene glycol; propylene glycol; 1,2-butanediol; 1,3-butanediol; 2,2,4-trimethyl-1,3-pentanediol; 1,5-pentanediol; 2,4-pentanediol; 1,6-hexanediol; 2,5-hexanediol; 2-methyl-1,3-pentanediol; 2-methyl-2,4-pentanediol; 2,4-heptanediol; 2-ethyl-1,3 hexanediol; 2,2-dimethyl-1,3-propanediol; 1,4-cyclohexanediol; 1,4-cyclohexanedimethanol; 1,2-bis(hydroxymethyl)cyclohexane; 1,2-bis(hydroxyethyl)cyclohexane; 2,2-dimethyl-3-hydroxypropyl-2,2-dimethyl-3-hydroxypropionate; diethylene glycol; dipropylene glycol; bis hydroxypropyl hydantoins; tris hydroxyethyl isocyanurate; the alkoxylation product of 1 mole of 2,2-bis(4-hydroxyphenyl)propane (i.e., bisphenol-A) and 2 moles of propylene oxide available as DOW-565 from DOW Chemical Company; and the like.

(b) Polyester polyols are generally known and prepared by conventional techniques utilizing simple diols, triols and higher hydric alcohols known in the art including but not limited to the previously described simpld diols, triols, and higher hydric alcohols (optionally in combination with monohydric alcohols) with polycarboxylic acids. Examples of suitable polycarboxylic acids include: phthalic acid; isophthalic acid; terephthalic acid; trimellitic acid; tetrahydrophthalic acid, hexahydrophthalic acid; tetrachlorophthalic acid; adipic acid, azelaic acid, sebacic acid; succinic acid; malic acid; glutaric acid; malonic acid; pimelic acid; suberic acid; 2,2-dimethylsuccinic acid; 3,3-dimethylglutaric acid; 2,2-dimethylglutaric acid; maleic acid, fumaric acid, itaconic acid; and the like. Anhydrides of the above acids, where they exist, can also be employed and are encompassed by the term "polycarboxylic acid". In addition, certain materials which react in a manner similar to acids to form polyester polyols are also useful. Such materials include lactones such as caprolactone, propylolactone and methyl caprolactone, and hydroxy acids such as hydroxycaproic acid and dimethylolpropionic acid. If a triol or higher hydric alcohol is used, a monocarboxylic acid, such as acetic acid and benzoic acid, may be used in the preparation of the polyester polyol, and for some purposes, such a polyester polyol may be desireable. Moreover polyester polyols are understood herein to include polyester polyols modified with fatty acids or glyceride oils of fatty acids (i.e., conventional alkyd polyols containing such modification). Another suitable polyester polyol is one prepared by reacting an alkylene oxide such as ethylene oxide, propylene oxide, butylglycidyl ether, and the glycidyl esters of organic acids such as CARDURA-E, with the carboxylic acid to form the corresponding ester.

Examples of the optional monohydric alcohols which may be used to prepare the polyester polyols include: ethanol, propanol, isopropanol, n-pentanol, neopentyl alcohol, 2-ethoxyethanol, 2-methoxyethanol, 1-hexanol, cyclohexanol, 2-methyl-2-hexanol, 2-ethylhexyl alcohol, 1-octanol, 2-octanol, 1-nonanol, 5-butyl-5-nonanol, isodecyl alcohol, and the like.

Alkyd polyols typically are produced by reacting polyhydric alcohols, polycarboxylic acids, and fatty acids derived from drying, semi-drying or non-drying oils in various proportions depending upon the extent of hydroxyl functionality and properties desired in the alkyd polyol. The techniques of preparing such alkyd polyols are well known generally. Usually, the process involves reacting together the polycarboxylic acid and fatty acid or partial glyceride thereof and the polyhydric alcohol (the latter usually in stoichiometric excess) in the presence of a catalyst such as litharge, sulfuric acid, or sulfonic acid to effect esterification with evolution of water. Examples of polyhydric alcohols typically used for preparation of the alkyd polyols include the simple diols, triols and higher hydric alcohols known in the art including but not limited to the previously described simple diols, triols, and higher hydric alcohols. Examples of polycarboxylic acids suitable for preparation of the alkyd polyols include those set forth previously in the description of polycarboxylic acids useful for preparing polyester polyols. Examples of suitable fatty acids include saturated and unsaturated acids such as stearic acid, oleic acid, ricinoleic acid, palmitic acid, linoleic acid, linolenic acid, licanic acid, elaeostearic acid, clupanodonic acid and mixtures thereof. The fatty acids may be in the form of the free acids with sufficient excess of the polyhydric alcohol being incorporated into the esterification mixture to compensate for their inclusion. However, in many instances, glyceride oils may be employed which have been partially alcoholized with sufficient amount of a polyhydric alcohol such as glycerol to supply the requisite amount of available hydroxyls for formation of the alkyd polyol.

(c) Polyether polyols are generally known. Examples of polyether polyols include the poly-(oxyethylene) glycols and poly-(oxypropylene) glycols prepared by the acid or base catalyzed addition of ethylene oxide or propylene oxide to initiators such as ethylene glycol, propylene glycol, diethylene glycol and dipropylene glycol and by the copolymerization of ethylene oxide and propylene oxide with initiator compounds such as trimethylolpropane, glycerol, pentaerythritol, sorbitol, sucrose and the like. Examples of polyether polyols also include the generally known poly-(oxytetramethylene) glycols prepared by the polymerization of tetrahydrofuran in the presence of Lewis acid catalysts such as boron trifluoride, tin (IV) chloride, antimony pentachloride, antimonytrichloride, phosphorous pentafluoride, and sulfonyl chloride. Other examples of polyether polyols include the generally known reaction products of 1,2-epoxide-containing compounds with polyols such as those included in the description of simple diols, triols, and higher hydric alcohols above.

(d) Amide-containing polyols are generally known and typically are prepared from any of the above-described diacids or lactones and diols, triols and higher alcohols, and diamines or aminoalcohols as illustrated, for example, by the reaction of neopentyl glycol, adipic acid and hexamethylenediamine. The amide-containing polyols also may be prepared through aminolysis by the reaction, for example, of carboxylates, carboxylic acids, or lactones with aminoalcohols. Examples of suitable diamines and aminoalcohols include hexamethylenediamine, ethylenediamine, phenylenediamines, toluenediamines, monoethanolamine, diethanolamine, N-methyl-monoethanolamine, isophorone diamine, 1,8-methanediamine and the like.

(e) Acrylic polyols include but are not limited to the known hydroxyl-functional addition polymers and copolymers of acrylic and methacrylic acids and their ester derivatives including but not limited to their hydroxyl-functional ester derivatives, acrylamide and methacrylamide, and unsaturated nitriles such as acrylonitrile and methacrylonitrile. Additional examples of acrylic monomers which can be addition polymerized to form acrylic polyols include hydroxyethyl (meth)acrylate, hydroxypropyl (meth)acrylate, methyl (meth)acrylate, ethyl (meth)acrylate, propyl (meth)acrylate, isopropyl (meth)acrylate, butyl (meth)acrylate, t-butyl (meth)acrylate, 2-ethylhexyl (meth)acrylate, n-hexyl (meth)acrylate, cyclohexyl (meth)acrylate, 3,3,5-trimethylcyclohexyl (meth)acrylate, decyl (meth)acrylate, isodecyl (meth)acrylate, lauryl (meth)acrylate, stearyl (meth)acrylate, phenyl (meth)acrylate, and isobornyl (meth)acrylate.

(f) Epoxy polyols are generally known and can be prepared, for example, by the reaction of glycidyl ethers of polyphenols such as the diglycidyl ether of 2,2-bis (4-hydroxyphenyl) propane, with polyphenols such as 2,2-bis (4-hydroxyphenyl) propane. Epoxy polyols of varying molecular weight and average hydroxyl functionality can be prepared depending upon the ratio of starting materials used.

(g) Polyhydric polyvinyl alcohols are generally known and can be prepared, for example, by the addition polymerization of vinyl acetate in the presence of suitable initiators followed by hydrolysis of at least a portion of the acetate moieties. In the hydrolysis process, hydroxyl groups are formed which are attached directly to the polymer backbone. In addition to homopolymers, copolymers of vinyl acetate and monomers such as vinyl chloride can be prepared and hydrolyzed in similar fashion to form polyhydric polyvinyl alcohol-polyvinyl chloride copolymers.

(h) Urethane polyols are generally known and can be prepared, for example, by reaction of an organic polyisocyanate with a polyol. Examples of polyisocyanates useful in the preparation of urethane polyols include those described above as exemplary of component (B) in the discussion of a preparation of NCO-functional compounds of the invention. Examples of polyols useful in the preparation of isocyanate prepolymers include those described in subsections (a) through (g) above.

Of the polyols described above for preparation of the NCO-terminated compounds of the invention utilizing isocyanate prepolymers, polyhydroxyl-functional esters and acrylic polyols are preferred, polyhydroxyl-functional esters being more preferred. The term "polyhydroxyl-functional esters" is intended to include both oligomeric ester polyols such as 2,2-dimethyl-3-hydroxypropyl-2,2-dimethyl-3-hydroxyproprionate and polyester polyols described above.

The mercapto-functional polyhydric alcohol and the vinyl-type silane typically are reacted, in the presence of the free radical initiator, to form the aforesaid addition product, in a separate step from reaction of the addition product with the organic polyisocyanate. Of course, it will be appreciated, given the disclosure herein, that the order of reacting the components can be varied. For example, the organic isocyanate may first be reacted with the mercapto-functional polyhydric alcohol to form a product, and thereafter the aforesaid product may be reacted with the vinyl silane monomer in the presence of a suitable free radical initiator. This illustrative alternate method may be suitable when it is desired also to incorporate moieties such as -NH-CO-S- in the NCO-terminated compounds of the invention.

It will be appreciated by one skilled in the art, given the disclosure herein, that the NCO-terminated compounds of the invention can be further chain extended with compounds containing active hydrogen atoms, examples of which include but are not limited to polyols such as, for example, those described herein previously.

It is to be understood that chain extension of the addition products of the invention with organic polyisocyanates can be carried out with additional polyols in the reaction mixture. Examples of such additional polyols include the polyols described herein previously as useful in the preparation of the isocyanate prepolymers and include: organic polyols in the broad classes including: (a) simple diols, triols, and higher hydric alcohols; (b) polyester polyols; (c) polyether polyols; (d) amide-containing polyols; (e) acrylic polyols; (f) epoxy polyols; (g) polyhydric polyvinyl alcohols; and (h) urethane polyols. If a stoichiometric excess of hydroxyl groups from the addition product of the invention (i.e., from the residue of the mercapto-functional polyhydric alcohol) and the additional polyol is employed, the resulting reaction product will contain hydroxyl functionality in addition to the silicon atoms bonded to hydrolyzable groups.

Addition products of the invention (namely the reaction products of the mercapto-functional polyhydric alcohols and vinyl-type silanes) can be utilized, for example, to prepare urethane resins which contain silicon atoms bonded to hydrolyzable groups which urethane resins can be cured in the presence of atmospheric moisture via reaction of the hydrolyzable groups with moisture. Moreover, the aforesaid urethane resins prepared utilizing addition products of the invention will contain moisture curable groups bonded to silicon atoms along the urethane polymer chain. This is to be contrasted with, for example, reaction products of organic polyols, organic polyisocyanates, and compounds such as isocyanatopropyltrimethoxysilane in which the hydrolyzable silyl groups tend to be at the chain ends of the polymer molecules.

The examples which follow are submitted for the purpose of further illustrating the nature of the invention and should not be construed as a limitation on the scope thereof.

As used in the body of the specification, examples, and claims, all percents, ratios and parts are by weight unless otherwise specifically indicated. Wherever used herein, "pbw" means "parts by weight".

EXAMPLE 1

This example illustrates in part (a) and (b) respectively: the preparation of addition product of a mercapto-functional polyhydric alchol and a vinyl silane having at least one hydrolyzable group directly attached to a silicon atom; and the preparation of an NCO-terminated compound which is the reaction product of the aforesaid addition product of a mercapto-functional polyhydric alcohol and a vinyl silane having at least one hydrolyzable group directly attached to a silicon atom, with an organic polyisocyanate.

(a) A reaction vessel equipped with thermometer, Dean Stark trap and means for maintaining a nitrogen blanket is charged with 118.5 g of vinyltrimethoxysilane and 133.4 g of methyl amyl ketone and heated to reflux under a blanket of nitrogen to a temperature of 95 degrees C. Next the addition of two charges are begun simultaneously to the contents of the vessel. Charge I consists of 91.5 g of mono-thioglycerine. Charge II consists of 2.0 g of 2,2'-azobis(2,4-dimethylvaleronitrile) (i.e., VAZO 67) dissolved in 25.0 g of methyl amyl ketone. Charges I and II are added to the contents of the vessel over a period of 1 hour while the temperature is maintained at about 95 degrees C. When the additions of charges I and II are complete 5.0 g of methyl amyl ketone is added to the contents of the vessel through the addition funnel used for charge I and 5.0 g of methyl amyl ketone is added through the addition funnel used for charge II. Thereafter the contents of the vessel are maintained at reflux for 1 hour at a temperature of about 95 degrees C. after which the contents of the vessel are cooled over a period of 15 minutes to a temperature of 60 degrees C. The product in the vessel at this point is an addition product of a mercapto-functional polyhydric alcohol and a vinyl silane having at least one hydrolyzable group directly attached to a silicon atom.

(b) Next, charge III consisting of 119.9 g of isophorone diisocyanate is added over a period of 15 minutes to the contents of the vessel while the temperature is maintained at about 60 degrees C. When the addition of charge III is complete 30.0 g of methyl amyl ketone is added to the contents of the vessel through the addition funnel used for charge III. Next the contents of the vessel are heated over 5 minutes to 65 degrees C. and thereafter over 1 hour and 40 minutes to 85 degrees C. Next the contents of the vessel are held at about 85 degrees C. for 1 hour after which the contents are heated over a period of 1 and ½ hours to a temperature of 110 degrees C. after which heating is discontinued and the contents of the vessel allowed to cool to room temperature. The resulting product at this point as determined by infrared spectroscopy is an NCO-terminated compound which is the reaction product of the aforesaid addition product of a mercapto-functional polyhydric alcohol and a vinyl silane having at least one hydrolyzable group directly attached to a silicon atom and an organic polyisocyanate.

(c) The resulting product of part (b) above is heated to 110 degrees C. and thereafter maintained in a temperature range of from 110 to 120 degrees C. for 6 hours after which heating is discontinued and the contents cooled to room temperature. Next, 8.0 g of methanol are added to the vessel.

The resulting product, having an NCO equivalent weight of 18,300 determined by infrared spectroscopy, is a urethane which can be cured, for example, by heating or by exposure at room temperature to atmospheric moisture.

(d) 20 g of the resulting product of part (c) above admixed with 0.1 g of dibutyltin dilaurate is applied with a 3 mil bar to 2 glass panels and one of the resulting films is allowed to cure at ambient temperature and the other at 110 degrees C. Both films cured to give tack-free, clear, rubbery coatings.

What is claimed is:

1. An addition product of a mercapto-functional polyhydric alcohol and a vinyl-type silane having at least one hydrolyzable group directly attached to a silicon atom, said addition product prepared by reacting said mercapto-functional polyhydric alcohol and said vinyl-type silane in the presence of a free radical initiator wherein said addition product is chain extended by reaction with an organic polyisocyanate.

2. The addition product of claim 1 wherein said organic polyisocyanate comprises an organic diisocyanate.

3. An NCO-terminated compound comprising the reaction product of:

(A) an addition product of a mercapto-functional polyhydric alcohol and a vinyl silane having at least one hydrolyzable group directly attached to a silicon atom, said addition product prepared by reacting said mercapto-functional polyhydric alcohol and said vinyl silane in the presence of a free radical initiator; and (B) an organic polyisocyanate.

4. The NCO-terminated compound of claim 3 wherein said hydrolyzable group, each of which may be the same or different, is selected from the group consisting of $-OR^1$,

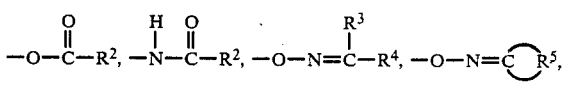

the monohydroxy $C_2$–$C_3$ residue of a 1,2- or 1,3-glycol, and the cyclic $C_2$–$C_3$ residue of a 1,2- or 1,3-glycol, wherein $R^1$ represents $C_1$–$C_4$ alkyl, $R^2$ independently represents H or $C_1$–$C_4$ alkyl, $R^3$ and $R^4$ independently represent H, $C_1$–$C_4$ alkyl, $C_6$–$C_8$ aryl and $R^5$ represents $C_4$–$C_7$ alkylene.

5. The NCO-terminated compound of claim 3 wherein said hydrolyzable group, each of which may be the same or different, represents a $C_1$–$C_4$ alkoxy group.

* * * * *